(12) United States Patent
Budhwani

(10) Patent No.: US 11,965,876 B1
(45) Date of Patent: *Apr. 23, 2024

(54) BIOMIMETIC INTERFACE DEVICE AND METHODS OF USING THE SAME

(71) Applicant: Karim I. Budhwani, Birmingham, AL (US)

(72) Inventor: Karim I. Budhwani, Birmingham, AL (US)

( * ) Notice: Subject to any disclaimer, the term of this patent is extended or adjusted under 35 U.S.C. 154(b) by 701 days.

This patent is subject to a terminal disclaimer.

(21) Appl. No.: 17/126,670

(22) Filed: Dec. 18, 2020

Related U.S. Application Data

(60) Continuation of application No. 16/145,818, filed on Sep. 28, 2018, now Pat. No. 10,969,383, which is a division of application No. 15/151,678, filed on May 11, 2016, now Pat. No. 10,114,010.

(60) Provisional application No. 62/159,606, filed on May 11, 2015.

(51) Int. Cl.
*C12M 1/00* (2006.01)
*C12M 3/00* (2006.01)
*G01N 33/50* (2006.01)

(52) U.S. Cl.
CPC ......... *G01N 33/5061* (2013.01); *C12M 21/08* (2013.01); *C12M 23/58* (2013.01); *C12M 29/00* (2013.01); *G01N 33/502* (2013.01)

(58) Field of Classification Search
None
See application file for complete search history.

(56) References Cited

U.S. PATENT DOCUMENTS

| | | | |
|---|---|---|---|
| 5,089,385 A | 2/1992 | Kiel | |
| 2009/0111180 A1 | 4/2009 | Vilendrer | |
| 2010/0041149 A1* | 2/2010 | Weidenbecher | C12M 29/04 435/395 |
| 2012/0034695 A1* | 2/2012 | Sethu | C12M 23/16 435/401 |
| 2014/0123728 A1 | 5/2014 | Mostowfi | |
| 2015/0004077 A1 | 1/2015 | Wikswo | |
| 2015/0065588 A1* | 3/2015 | Weinberger | C12M 23/42 506/10 |
| 2016/0040107 A1 | 2/2016 | Hedberg | |
| 2016/0313306 A1 | 10/2016 | Ingber | |

OTHER PUBLICATIONS

Jang et al. Human Kidney Proximal Tubule-On-A-Chip for a Drug Transport and Nephrotoxicity Assessment; Inetgrative Biology, vol. 5 (2013) pp. 1119-1129.

(Continued)

*Primary Examiner* — Holly Kipouros
(74) *Attorney, Agent, or Firm* — C. Brandon Browning; Maynard Nexsen PC

(57) ABSTRACT

The present disclosure generally pertains to a biomimetic apparatus configured to simulate physiological conditions by, in part, providing for both barrier and transport interfaces. The presently disclosed apparatus may be used to: test therapeutics for different diseases; to study transport; form a substrate for any organ tissue with a barrier and/or transport function; provide a closed loop assembly for fluid flow; mimic underlying and enveloped tissue; and model external environmental conditions.

14 Claims, 4 Drawing Sheets

(56) References Cited

OTHER PUBLICATIONS

Lee et al. Hydrophilic Electrospun Polyurethane Nanofiber Matrices for HMSC Culture in a Microfluidic Cell Chip; Journal of Biomedical Materials Research Part A, vol. 90, No. 2 (2008) pp. 619-628.
Yum et al. Physiologically Relevant Organs on Chips; vol. 9, No. 1 (2014) pp. 16-27.

* cited by examiner (A)

BIOMIMETIC INTERFACE DEVICE AND METHODS OF USING THE SAME

CROSS REFERENCE TO RELATED APPLICATION

This application is a continuation of and claims priority to U.S. patent application Ser. No. 16/145,818, titled "BIOMIMETIC INTERFACE DEVICE AND METHODS OF USING THE SAME," filed on Sep. 28, 2018, which is a divisional of U.S. patent application Ser. No. 15/151,678, titled "BIOMIMETIC INTERFACE DEVICE AND METHODS OF USING THE SAME," filed on May 11, 2016, now U.S. Pat. No. 10,114,010, and U.S. Provisional Patent Application No. 62/159,606, entitled "Lab-on-a-Brane: A simple and inexpensive, but highly effective, physiological barrier interface on spun biological or synthetic elastomer scaffold with configuration flexibility including acellular, cellular, multicellular, ECM-cellular" filed on May 11, 2015, the entire contents of which are incorporated herein by reference.

BACKGROUND OF THE INVENTION

Improved treatment options for diseases require new drug development. Drug research and development, however, remain expensive and slow in large part due to inadequate methods for modeling diseases and evaluating potential therapeutics. Animal models, although widely used for such evaluations, raise numerous ethical concerns and are an imperfect medium for such research. In fact, approximately 90% of the therapeutics that succeed in animal models subsequently fail to advance through human trials. Therefore, efforts have been ongoing to engineer an in vitro environment that is configured to mimic, in vivo, human physiological conditions.

Efforts to engineer such environments remain inadequate. Cells in conventional, static culture dishes, for example, are not physiologically suitable for modeling blood vessels—the primary pharmacokinetic interface—because vascular cells cultured in the absence of appropriate hemodynamic stresses, such as shear, pressure, and stretch, fail to mimic the phenotype and function of cells from intact vessels. Many current or proposed solutions address just one of many variables necessary for suitable evaluation of therapeutics. For example, such current or proposed devices: (a) support only single cell systems; (b) do not provide any interfacial function; (c) provide interfacial function that is not configurable for perfusion; (d) are unable to mimic the layered architecture characteristic of various organ tissues performing barrier, transport, or both functions; and/or (e) are too complex or too expensive for widespread adoption.

SUMMARY OF THE INVENTION

In one embodiment, the present disclosure relates to a physiologically-relevant apparatus including: at least one cassette; wherein each cassette includes a spun elastomer scaffold located within a channel separating two chambers, the spun elastomer scaffold, channel and chambers being sealed within the cassette; wherein each chamber in each cassette includes a port and nozzle configured to connect each chamber to tubing; wherein the tubing is connected to a pump; wherein the pump is configured to flow fluid in a circuit through the tubing and each cassette. In certain embodiments, the apparatus further includes at least one one-way fluid flow valve connected to the tubing. In certain embodiments, the apparatus further includes at least one reservoir connected to the tubing. In certain embodiments, the apparatus further includes at least one sensor connected to the tubing. In certain embodiments, the at least one sensor is configured to measure pressure waves. In certain embodiments, the at least one sensor is configured to measure flow rate. In certain embodiments, at least two cassettes are connected in series. In certain embodiments, at least two cassettes are connected in parallel. In certain embodiments, each spun elastomer scaffold is seeded with a biological sample. In certain embodiments, the biological sample is human cells. In certain embodiments, the human cells are smooth muscle cells. In certain embodiments, the spun elastomer scaffold is self-riveted to chambers.

In another embodiment, the present disclosure relates to a method of using the apparatus to evaluate pharmacokinetics of potential therapeutics. In certain embodiments, the present disclosure relates to a method including the steps of seeding a spun elastomer scaffold in the apparatus with a biological sample; configuring the apparatus pump to create a specified flow rate and pressure; adding an analyte to a reservoir; flowing a fluid through the apparatus for a specified period of time; and measuring the analyte. In certain embodiments, the analyte is measured in a second reservoir. In certain embodiments, the analyte is measured in at least one chamber of at least one cassette. In certain embodiments, the biological sample comprises human cells. In certain embodiments, the human cells comprise of smooth muscle cells. In certain embodiments, the analyte is a pharmaceutical. In certain embodiments, the analyte is a biological sample.

BRIEF DESCRIPTION OF THE FIGURES

The disclosure can be better understood with reference to the following figures.

DETAILED DESCRIPTION OF THE INVENTION

The present disclosure generally pertains to a biomimetic apparatus configured to simulate physiological conditions. The presently-disclosed apparatus is configured to simulate such physiological conditions by, in part, providing for both barrier and transport interfaces. The presently disclosed apparatus may be used to: test therapeutics for different diseases; study transport; form a substrate for any organ tissue with a barrier and/or transport function; provide a closed loop assembly for fluid flow; mimic underlying and enveloped tissue; and model external environmental conditions.

As used herein, "analyte" means a specific chemical or biological material or compound that is to be measured.

As used herein, "biological sample" means biological samples known in the art including, but not limited to, cells, proteins and lipids.

As used herein, "elastomer" means an elastic polymer including, but not limited to, polydimethylsiloxane and other elastic polymers known in the art.

As used herein, "nozzle" means a device, component, or combination of components used to pass (either actively or passively), inject, or expel fluid.

As used herein, "pharmaceutical" means articles intended for use in the diagnosis, cure, mitigation, treatment or prevention of disease or biological disorders in mammals, including humans.

As used herein, "reservoir" means a chamber capable of containing fluid. Reservoirs include, but are not limited to, conical tubes, beakers, and other chambers capable of forming an airtight and watertight seal.

As used herein, "seeding" means the process of introducing cells or other biological sample into adherent material, for example, a spun elastomer scaffold, such that the cells or biological sample can attach to the material.

As used herein, "tubing" means tubing, pipe, casing, cylindrical pipe or the equivalent configured to allow the flow of fluid. Tubing may be composed of rubber, metal, or other material known in the art capable of forming a watertight and airtight seal when connected to a port or nozzle.

Figure 1:
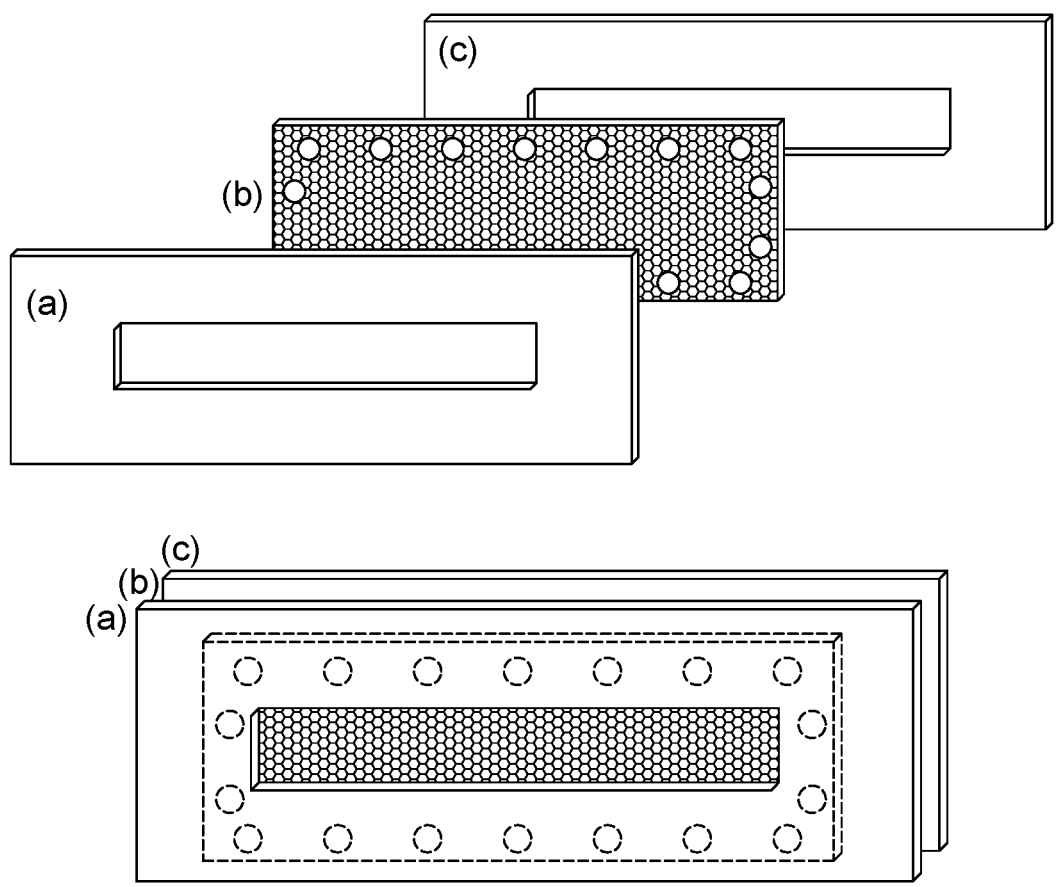
FIG. 1 is an illustration of an exemplary embodiment of a spun elastomer scaffold, identified as layer (b), sandwiched between two cast chambers, identified as layers (a) and (c), to form the central cassette. Approximately 500 μm diameter holes are bored on edges and corners of the spun elastomer scaffold for securely self-riveting it to the two chambers.
Figure 2:
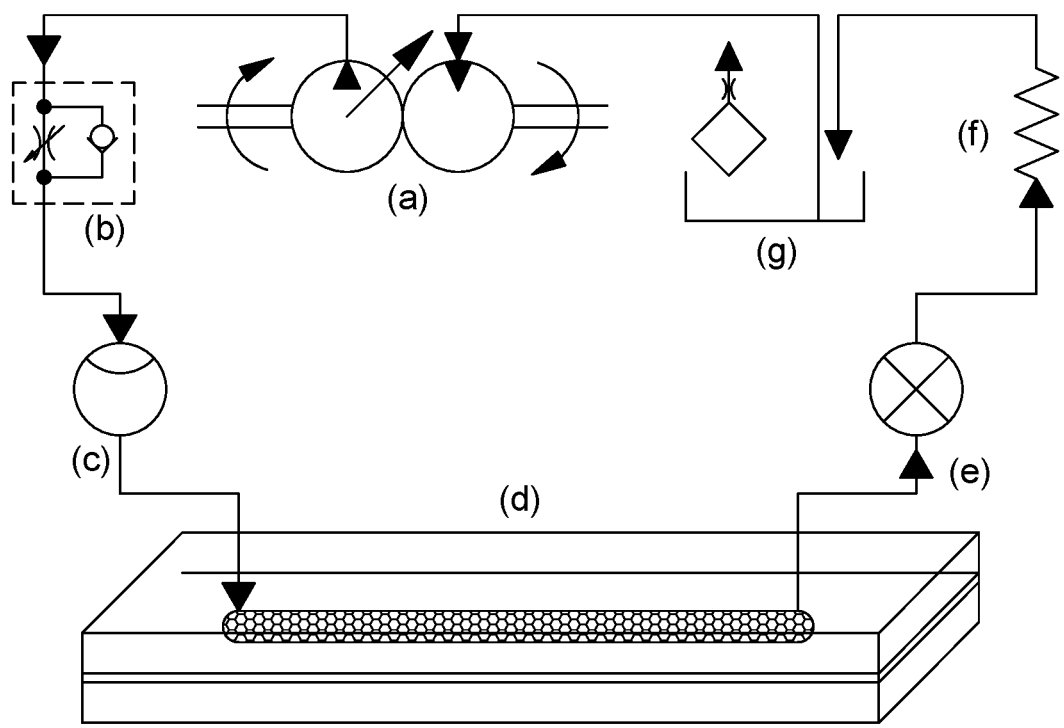
FIG. 2 is an illustration depicting an exemplary embodiment of the disclosed apparatus that includes one or more cassettes (d), a pump (a), a one-way valve (b), a flow sensor (c), a pressure sensor (e), resistance (f), and perfusion media (g).
Figure 3:
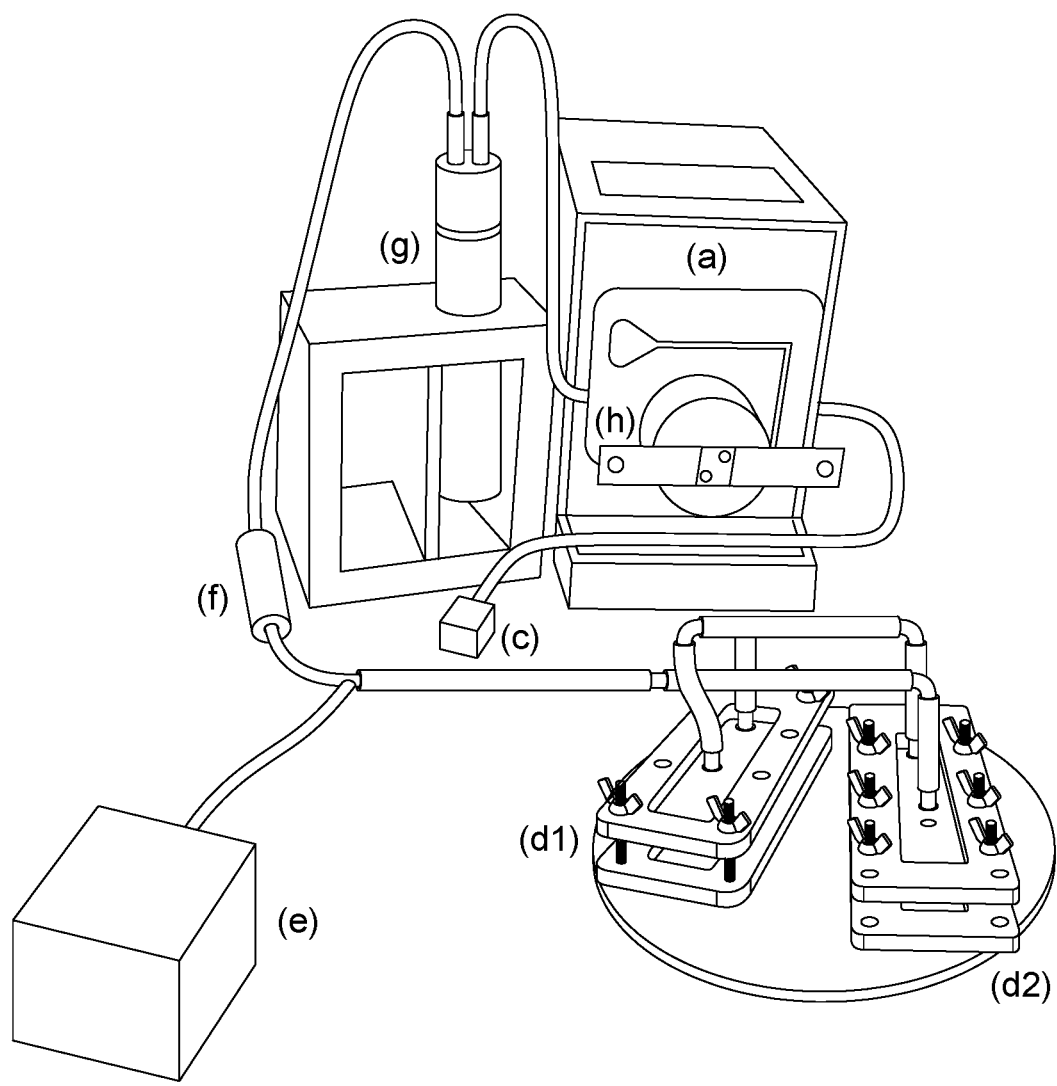
FIG. 3 is an image of an exemplary embodiment of the disclosed apparatus with two cassettes (d1 and d2) connected in series, a configurable pump (a), resistance (f) and fluid flow guide (h), sensors (c and e), and a reservoir (g).

In certain embodiments, the present disclosure relates to an apparatus including: a spun elastomer scaffold (see, e.g., FIG. 1(b)); at least one chamber (see, e.g., FIGS. 1(a) and 1(c)) in at least one case (together, with the scaffold and at least one chamber, forming a cassette; see, e.g., FIGS. 3(d1) and 3(d2)); tubing for fluid flow; a configurable pump (see, e.g., FIGS. 2(a) and 3(a)); and at least one reservoir (see, e.g., FIG. 3(g)). In certain embodiments, each chamber and case is composed of elastomer. In certain embodiments, the at least one chamber is cast. In other embodiments, the at least one chamber is bored or drilled. In certain embodiments, the disclosed apparatus further includes at least one fluid flow guide or valve (see, e.g., FIGS. 2(b) and 3(h)). In certain embodiments, the one or more fluid flow guide or valve is configured to prevent reverse flow (see, e.g., FIG. 2, which depicts one-way flow within an exemplary embodiment of the apparatus). In certain embodiments, the disclosed apparatus further comprises at least one sensor (see, e.g., FIGS. 3(c) and 3(e)). In certain embodiments, at least one sensor is configured to measure pressure waves. In certain embodiments, at least one sensor is configured to measure flow rate. In certain embodiments, at least one cassette is reusable. In certain embodiments, the apparatus is filled with a sterile solution. In certain embodiments, the solution is cell culture media. Cell culture media suitable for particular cell types is known in the art.

Figure 4:
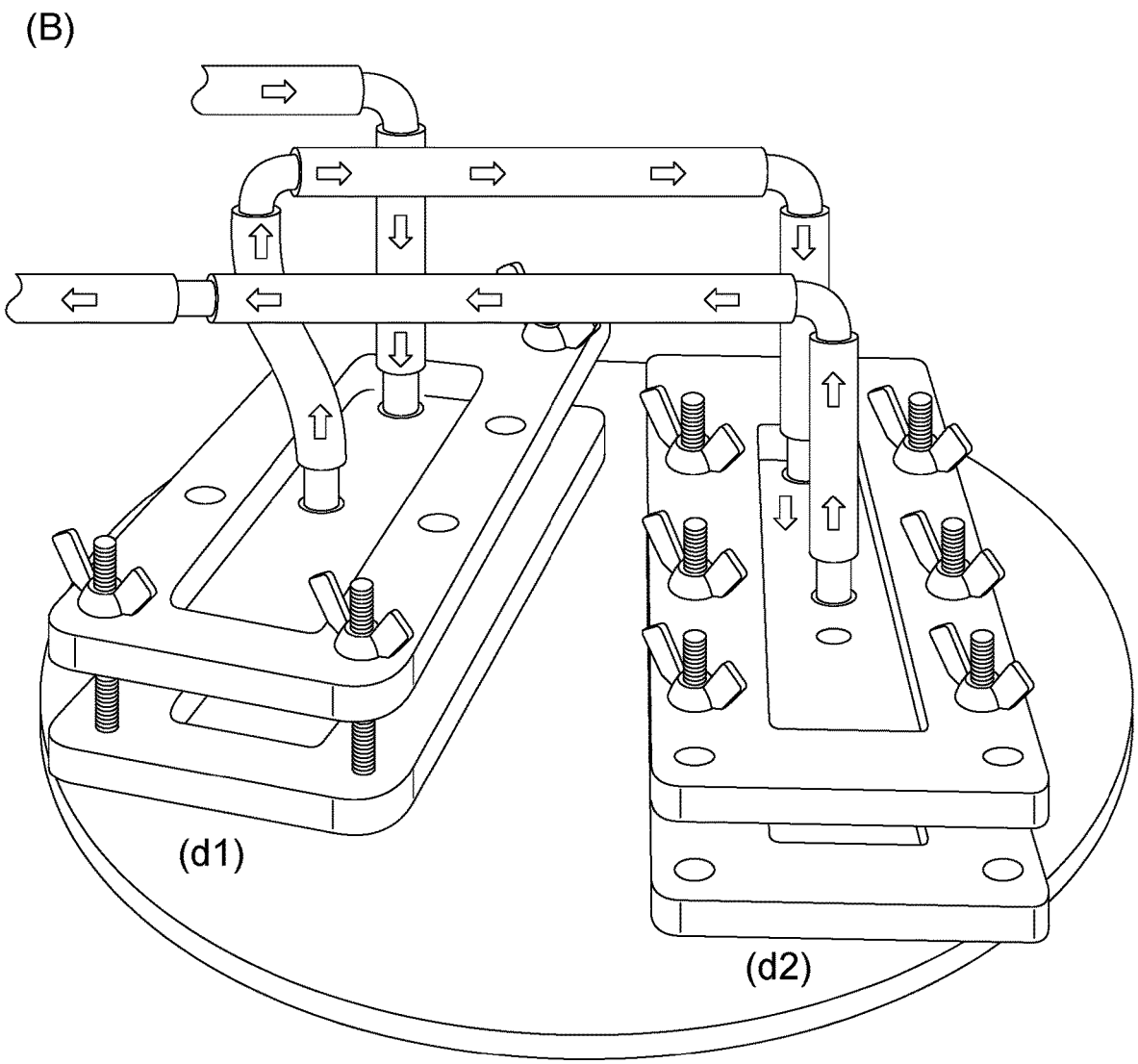
FIG. 4 is an image of an alternative perspective of the exemplary embodiment of the disclosed apparatus with two cassettes (d1 and d2) shown in series configuration, each cassette including a spun elastomer scaffold sandwiched between two cast chambers cultured and subsequently encased in reusable case.

In other embodiments, at least two cassettes can be connected in series (see, e.g., d1 and d2 in FIGS. 3 and 4), parallel, or any combination to rapidly and easily scale the platform. For example, in certain embodiments, two cassettes may be connected in series such that tubing connected to a pump connects to the nozzle of one chamber of a first cassette, tubing connects the second chamber of the first cassette to one chamber of a second cassette, and tubing connects the second chamber of the second cassette to the pump. In another example, in certain embodiments, two cassettes may be connected in parallel such that tubing connected to a pump splits into two lines of tubing, each line of tubing connecting to a first chamber of a cassette, and each second chamber of each cassette connecting to tubing connecting to the pump.

In other embodiments, for highly parallel applications, such as personalized and/or precision medicine, the disclosed apparatus further includes a computer system configured to manage and monitor the platform. In other embodiments, the computer system is configured to perform data analysis.

In certain embodiments, the spun elastomer scaffold separates at least two chambers, through which in vivo conditions may be simulated in the presence of fluid flow. In certain embodiments, a cassette comprises a case, which contains two chambers separated by a channel configured to fit a spun elastomer scaffold. In certain embodiments, each case includes a lower and upper housing, wherein the lower housing includes cavities for two chambers connected by a channel, and wherein the upper housing includes a port (i.e., an opening in the housing) positioned above each chamber when the upper and lower housings are connected by a watertight and airtight seal. In certain embodiments, the case is fabricated from elastomer using methods known in the art. In certain embodiments, each port is configured to connect to tubing. In certain embodiments, the port includes a nozzle protruding from the cassette configured to connect to tubing (see, e.g., FIGS. 3 and 4), such connection forming a watertight and airtight seal. In certain embodiments, each nozzle is formed from the upper housing of a cassette. In other embodiments, each nozzle is fabricated separately from the upper housing of a cassette and affixed to a port. In certain embodiments, the apparatus includes at least one valve to control the direction of flow. In certain embodiments, each valve includes nozzles configured to connect to, and form a watertight and airtight seal with, tubing.

In certain embodiments of the apparatus, tubing connects a cassette to a pump, at least one sensor is configured to measure dynamic conditions and at least one reservoir is connected to the tubing. In certain embodiments, at least one reservoir is sealed with a stopper through which stopper tubing may be inserted such that one end of tubing protrudes into the reservoir and deposits fluid while a second end of tubing protrudes into the reservoir to draw in fluid, thereby maintain fluid flow through the apparatus. In certain embodiments, at least one reservoir contains a stopper through which a needle of a syringe or other equivalent tool may be inserted to allow injection (addition) of an analyte to the reservoir or, alternatively, the drawing of fluid from the reservoir.

In certain embodiments, the apparatus is configured to simulate fluid to cell interactions between two chambers. In other embodiments, the apparatus is configured to simulate fluid to fluid interactions between two chambers. In certain embodiments, the apparatus is configured to simulate in vivo conditions including pressure, flow, shear, and stretch forces, essential to maintaining vascular cell phenotype and function. In certain embodiments, the apparatus is configured to simulate and to monitor filtration functions, nutrient delivery and waste extraction, conditions such as hypoxia, healthy and pathological tissue (tumor) dynamics, environmental hazards and/or thresholds for radiation, gravity, and elevation.

In an exemplary embodiment of the disclosed apparatus, an elastomer scaffold is spun on one side of an chamber. In certain embodiments, an elastomer scaffold is spun wherein the diameter of the elastomer fibers is about the diameter of extracellular matrix fibers. An elastomer scaffold may be fabricated by electrospinning, as known in the art. See, e.g., Li, et al. J Biomed Mater Res. 2002 Jun. 15; 60(4):613-21. For example, nylon 6 pellets may be dissolved in 1,1,1,3, 3,3-hexafluoro2-propanol (HFP) to obtain about a 10% wt solution. Collagen (e.g., freeze-dried soluble calf-skin collagen sponge) and collagen+polyester (PLLA) solutions for spinning were prepared in the same way, but using a 50:50 weight ratio of collagen and polyester pellets in HFP to obtain a concentration of about 10% wt. The resultant solution may be spun onto fabricated chambers to form a thin fibrous membrane. A total volume of about 1.5 ml may be spun into fibers over the about 10 cm×20 cm area to form fibrous membranes with fiber diameter approximating extracellular matrix fibers. The spinning device orientation may be changed from vertical to horizontal about every fifteen minutes. The chambers may then be moved to a vacuum desiccator and allowed to dry overnight. Alternatively, fibrous membranes may be spun on patterned surrogate substrates, dried, transferred to sterile paper backing, cut in about 30 mm×8 mm rectangular pieces, and manually centered over the channels in chambers. Prior to self-riveting, any paper backings should be peeled off.

The chamber with the spun elastomer scaffold is irreversibly bonded to another chamber, which lacks a spun elastomer scaffold, in an invertible sandwich architecture by a self-rivet mechanism so that the substrate membrane is suspended in between the two chambers in a watertight and airtight seal. The rivet may be formed by boring holes of about 500 µm diameter along the edges and on the corners of the spun scaffold (see, e.g., FIG. 1(b)) to expose the underlying elastomer for self-riveting. The scaffold may be brought in conformal contact with two chambers, ensuring alignment of channels, clamped and cured at about 70° C. for about ninety minutes to bond the sandwiched membrane in a watertight seal. In an alternative embodiment, an elastomer scaffold is spun on a surrogate substrate in lieu of being spun on one side of a chamber.

In certain embodiments, biological components are adsorbed, bonded, or grown on the spun elastomer scaffold in the apparatus. In embodiments with multiple cassettes, the biological components may be different for each spun elastomer scaffold. In certain embodiments, biological components are human cells. In certain embodiments, the human cells are smooth muscle cells. Methods of seeding cells onto a scaffold are known in the art. For example, before seeding with cells, a cassette may be sterilized using ethanol, dried, and placed under UV radiation. Attachment factor, fibronectin, and gelatin may then be deposited on the scaffold and allowed to adsorb overnight at 4° C. The cassette may then be placed in a 37° C., 5% CO2, humidified incubator for about one hour prior to seeding. Cells may be seeded on prepared cassettes and incubated at 37° C., 5% CO2 for at least twenty-four hours. The media from each cassette may then be aspirated, replaced by a solution of media and adhesion factor, and placed in 37° C., 5% CO2, humidified incubator for about five minutes. Media and adhesion factor solution may then be aspirated and the scaffold may be seeded a second time with resuspended cells from a confluent culture and placed in 37° C., 5% CO2, humidified incubator for at least twenty-four hours.

In certain embodiments, the apparatus is sterilized prior to the adsorption, bonding or growth of biological components on the spun elastomer scaffold. Methods of sterilization are known in the art and include, but are not limited to, application of ethanol and exposure to UV radiation.

In certain embodiments, the spun elastomer scaffold may be loaded in the cassette and integrated into the loop, thereby configured to simulate specified physiological and/or environmental dynamics. For example, a pump may be configured to create a flow rate and pressure specified by a user to simulate an in vivo flow rate and pressure, such flow rate and pressure monitored by sensors within the apparatus.

One advantage of the presently-disclosed apparatus is the modular nature of the apparatus. Such modularity allows the presently-disclosed apparatus to be reconfigured, among other applications, for (a) evaluating new molecular targets, (b) evaluating molecular targets under specific and/or triggered conditions, (c) evaluating repurposed or off-patent therapies to treat other conditions, (d) computing and subsequently administering specific compounds, dosages, and so on for individual patients also referred to as personalized medicine, (e) similar configurations can be used for the genomics based counterpart in precision medicine, (f) understanding the molecular, for instance, basis of diseases, (g) subsequently developing therapies for these diseases and conditions, (h) assessing the impact of environmental conditions such as zero gravity, radiation, and others on uptake and tissue, (i) toxicology, (j) inflammation, (k) ex vivo device-animal and device-human interface, (l) biological water filtration systems, (m) advancement of basic science, (n) environmental control for hospital or industrial air quality, and more.

In another embodiment, the present disclosure contemplates a method of using an embodiment of the disclosed apparatus, which includes at least one one-way flow valve, to measure an analyte comprising the steps of: (a) adding an analyte to a reservoir upstream (relative to the one-way fluid flow) of the at least one cassette; (b) running a pump for a specified period of time to allow fluid to flow through the apparatus; and (c) extraction of fluid from a second reservoir located downstream from the at least one cassette. In such embodiment, the analyte would be required to pass through the at least one cassette to reach the second "downstream" reservoir.

The presently disclosed apparatus, by virtue of being physiologically-relevant (i.e., by simulating in vivo conditions), is suitable for the testing the kinetics of analytes for a variety of diseases including, but not limited to, cancer, cardiovascular disease, and other diseases and conditions, thereby giving researchers and clinicians a valuable tool to assist with research and development for a disease or condition of interest.

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

The methodologies and the various embodiments thereof described herein are exemplary. Various other embodiments of the methodologies described herein are possible.

Now, therefore, the following is claimed:
1. A physiologically-relevant apparatus comprising:
  at least one cassette;
  wherein each cassette includes a spun elastomer scaffold
    located within a channel separating two chambers;

wherein the spun elastomer scaffold, the channel and the two chambers are sealed within the cassette;

wherein each chamber in each cassette includes a port and nozzle configured to connect each chamber to tubing;

wherein each chamber forms a portion of a fluid circuit;

wherein the spun elastomer scaffold includes a plurality of holes configured for allowing self-riveting the spun elastomer scaffold between to the two chambers; and wherein each hole of the plurality of holes serves to hold the spun elastomer scaffold in place between the two chambers.

2. The apparatus of claim 1, further comprising at least one one-way fluid flow valve connected to the tubing.

3. The apparatus of claim 1, further comprising at least one reservoir connected to the tubing.

4. The apparatus of claim 1, further comprising at least one sensor connected to the tubing.

5. The apparatus of claim 1, wherein at least two cassettes are connected in series.

6. The apparatus of claim 1, wherein at least two cassettes are connected in parallel.

7. The apparatus of claim 1, wherein each spun elastomer scaffold is seeded with a biological sample.

8. The apparatus of claim 7, wherein the biological sample is animal cells.

9. A physiologically-relevant apparatus comprising:
a cassette;
wherein the cassette includes a scaffold located within a channel separating two chambers, the scaffold, the channel and the two chambers being sealed within the cassette;
wherein each chamber in the cassette includes a port and nozzle configured for connecting each chamber to a fluid circuit;
wherein the scaffold includes a plurality of holes formed configured for self-riveting the scaffold between the chambers, and
wherein the plurality of holes serve to hold the scaffold in place between the two chambers.

10. The apparatus of claim 9, wherein the scaffold is a spun scaffold.

11. The apparatus of claim 9, including tubing fluidly coupled between the nozzle and a pump configured for causing fluid to flow in the circuit through the tubing and the cassette.

12. The apparatus of claim 9, wherein the scaffold is a spun elastomeric scaffold.

13. The apparatus of claim 9, wherein the chambers are self-riveted to one another through the plurality of holes.

14. The apparatus of claim 13, wherein plurality of holes are located along edges of the scaffold.

* * * * *